United States Patent
Aso

(10) Patent No.: US 6,942,792 B2
(45) Date of Patent: Sep. 13, 2005

(54) MIXER FOR LIQUID CHROMATOGRAPH

(75) Inventor: Yoshiaki Aso, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/637,153

(22) Filed: Aug. 8, 2003

(65) Prior Publication Data

US 2004/0042340 A1 Mar. 4, 2004

(30) Foreign Application Priority Data

Aug. 28, 2002 (JP) .......................... 2002-248482

(51) Int. Cl.$^7$ .............................................. B01D 15/08
(52) U.S. Cl. ..................... 210/198.2; 210/101; 210/656; 366/340; 366/341; 366/336; 366/DIG. 3
(58) Field of Search .............................. 210/101, 198.2, 210/656; 366/341, 336, 340, DIG. 3

(56) References Cited

U.S. PATENT DOCUMENTS

| | | | | |
|---|---|---|---|---|
| 3,856,270 A | * | 12/1974 | Hemker ...................... 366/340 |
| 3,881,701 A | * | 5/1975 | Schoenman et al. ........ 239/403 |
| 5,640,995 A | * | 6/1997 | Packard et al. ............. 137/597 |
| 5,690,763 A | * | 11/1997 | Ashmead et al. ............. 156/60 |
| 5,698,299 A | * | 12/1997 | Schmidt et al. ............. 428/209 |
| 5,846,396 A | * | 12/1998 | Zanzucchi et al. .......... 204/601 |
| 5,849,208 A | * | 12/1998 | Hayes et al. ................... 216/94 |
| 5,882,571 A | * | 3/1999 | Kaltenbach et al. ......... 264/400 |
| 5,904,424 A | * | 5/1999 | Schwesinger et al. ....... 366/336 |
| 5,985,119 A | * | 11/1999 | Zanzucchi et al. .......... 204/450 |
| 6,136,272 A | * | 10/2000 | Weigl et al. ............. 422/82.05 |
| 6,190,034 B1 | * | 2/2001 | Nielsen et al. ............... 366/336 |
| 6,494,614 B1 | * | 12/2002 | Bennett et al. .............. 366/336 |
| 6,537,506 B1 | * | 3/2003 | Schwalbe et al. ........... 422/130 |
| 6,623,860 B2 | * | 9/2003 | Hu et al. .................. 428/411.1 |
| 6,676,835 B2 | * | 1/2004 | O'Connor et al. ........... 210/542 |
| 2002/0192701 A1 | * | 12/2002 | Adey ............................ 435/6 |
| 2003/0123322 A1 | * | 7/2003 | Chung et al. ............. 366/165.1 |

FOREIGN PATENT DOCUMENTS

| | | |
|---|---|---|
| CN | 1140134 A | 1/1997 |
| JP | 2003-156481 | 5/2003 |

* cited by examiner

Primary Examiner—Ernest G. Therkorn
(74) Attorney, Agent, or Firm—Rankin, Hill, Porter & Clark LLP

(57) ABSTRACT

Three metal plate materials, each having penetration holes, are united together in this order as a set at such positions that penetration holes can penetrate through the three metal plate materials so as to form a mixing portion. A plurality of sets, each having the mixing portion, are integrated together at such positions that all of the penetration holes can penetrate through the respective sets of plate materials. The mixing portions of the respective sets are connected in parallel to one another.

10 Claims, 3 Drawing Sheets

MIXER FOR LIQUID CHROMATOGRAPH

BACKGROUND OF THE INVENTION

1. Field of the Invention

The present invention relates to a mixer for a liquid chromatograph and, in particular, to a mixer which is used to mix liquids together so as to make an eluent for gradient analysis.

2. Description of the Related Art

In a liquid chromatograph, there is made a gradient analysis in which the composition of an eluent is caused to vary continuously or in a stepped manner. In the gradient analysis, in order that two or more kinds of liquids are mixed together to thereby introduce a column as an eluent, a gradient eluting apparatus includes a mixer for mixing a plurality of liquids together. As the mixer, there is often used an apparatus of a flow-through type which does not include a movable part; for example, there is known an apparatus structured such that balls made of stainless steel are loaded into a pipe having an inside diameter of about 3 mm and a length of about 50 mm. This type of mixer is composed of a plurality of machined parts such as entrance and exit machined parts. In the case of such mixer, since balls for mixing are loaded into the interior of the mixer, the internal capacity thereof is large. In order to mix together the plurality of liquids with high efficiency, there is required the optimum mixer capacity according to the flow quantities of the liquids; however, a flow passage for such mixture depends on the balls loaded into the interior of the pipe, which makes it impossible to form a desired flow passage. In addition, this type of mixer is complicated in machining and assembling, which results in the high cost thereof.

SUMMARY OF THE INVENTION

The present invention aims at eliminating the above-mentioned drawbacks found in the related-art mixer. Accordingly, it is an object of the invention to provide a mixer which can provide excellent mixing performance, can be reduced in size, and can change the mixing capacity thereof easily.

In attaining the above object, according to the invention, there is provided a mixer for a liquid chromatograph comprising:

a connected body including a plurality of plate materials connected together so as to form therein flow passages serving as a mixing portion, the connected body including at least two liquid supply holes for supplying liquids to the flow passages and a take-out hole for taking out the liquids mixed together from the flow passages, wherein two or more plate materials each including a flow passage are superimposed on top of each other and two or more of the flow passages are connected in parallel to each other.

The series connection of the mixing portions is unable to enhance the liquid mixing efficiency sufficiently and, in order to be able to enhance the liquid mixing efficiency sufficiently, the mixing portions must be connected in parallel to one another. According to the invention, by superimposing a plurality of plate materials on top of one another, each having a flow passage serving as a mixing portion therein, the flow passages can be connected together in parallel. For the parallel arrangement of the flow passages, there may be used three plate materials as a set. That is, a first plate material has penetration holes for supply of the liquids and a penetration hole for taking out the mixed liquids. A second plate material has penetration holes for supply of the liquids, a penetration hole for taking out the mixed liquids, and a flow passage for mixing the liquids together. A third plate material has penetration holes for supply of the liquids, a penetration hole for taking out the mixed liquids, and a flow passage for collecting the mixed liquids together. The penetration holes for supply of the liquids and the penetration holes for taking out the mixed liquids of the respective plate materials are formed at the same positions, thereby providing a structure in which these penetration holes penetrate through the three plate materials. A plurality of sets, each composed of the three plate materials, are connected together in such a manner that the penetration holes for supply of the liquids and the penetration holes for taking out the mixed liquids are set at the same positions. Thanks to this, the respective sets (i.e., the mixing portions of the respective sets) can be connected in parallel to one another and, after the supplied liquids are mixed together in the flow passages of their respective sets, they can be collected together by the common take-out penetration hole.

DETAILED DESCRIPTION OF THE INVENTION

Figure 1:
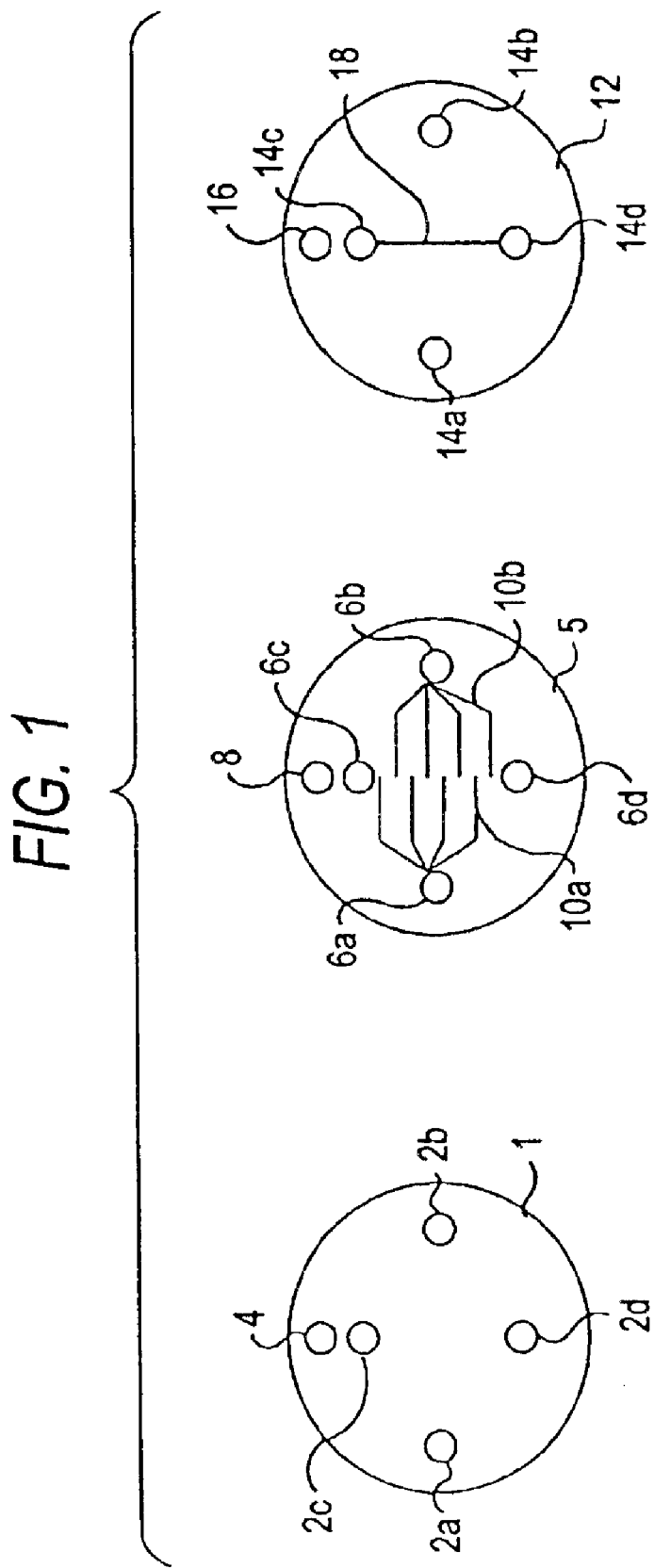
FIG. 1 is a schematic structure view of an embodiment of a mixing portion formed in a mixer for a liquid chromatograph according to the invention.

Now, description will be given below in detail of the mode for carrying out the invention with reference to the accompanying drawings. FIG. 1 is a schematic structure view of an embodiment of a mixing portion of a mixer for a liquid chromatograph according to the invention. Three metal plate materials 1, 5, and 12 provide a basic structure for the mixing portion. The metal plate material 1 includes four penetration holes 2a–2d and a positioning hole 4. The metal plate material 5 includes four penetration holes 6a–6d, a positioning hole 8, and two flow passages 10a, 10b. The metal plate material 12 includes four penetration holes 14a–14d, a positioning hole 16 and a flow passage 18. The metal plate materials 1, 5, and 12 are each a corrosion resistant metal plate (for example, SUS316) having a thickness of 2 mm or less. The positioning holes 4, 8 and 16 are all penetration holes and are respectively formed at the same positions in their associated metal plate materials 1, 5 and 12. Also, the penetration holes 2a–2d, 6a–6d, and 14a–14d are respectively formed at the same positions in their associated metal plate materials 1, 5 and 12.

The metal plate materials 1, 5 and 12 are united together in this order, as a set, using the positioning holes 4, 8 and 16, at such determined positions that the penetration holes 2a–2d, 6a–6d, and 14a–14d can penetrate through the three metal plate materials 1, 5 and 12; that is, there is formed a mixing portion. Further, a plurality of sets, each having the same combination of the metal plate materials 1, 5 and 12 forming the mixing portion, are united together at such determined positions that the penetration holes 2a–2d, 6a–6d, and 14a–14d can penetrate through their associated set of plate materials. Next, on the metal plate material 12 of the set of plate materials that are combined last, there is placed a flat plate including neither flow passage nor penetration hole. Two kinds of liquids are introduced from the penetration holes 2a and 2b, and reach the penetration holed 6a and 6b, while the liquids in part flow to the flow passages 10a and 10b. The flow passages 10a and 10b are grooves which are formed so as to penetrate through the metal plate material 5. The liquids, which have flown through the flow passages 10a and 10b, meet together in the flow passage 18 so that the two kinds of liquids are mixed together. The flow passage 18 is a groove which has a bottom. The mixed liquids are allowed to flow from the penetration holes 14c and 14d and flow through the penetration holes 6c and 6d, and are taken out from the penetration holed 2c and 2d.

The liquids, which have passed through the penetration holes 2a, 2b, 6a, 6b and 14a, 14b of the mixing portion of a first set, are introduced in the penetration holed 2a and 2b of the mixing portion of a second set and reach the penetration holes 6a and 6b, while the liquids in part flow to the flow passages 10a and 10b. In the mixing portion of the second set as well, similarly to the mixing portion of the first set, the liquids are mixed together and, finally, the thus mixed liquids are taken out from the penetration holes 2c and 2d of the mixing portion of the first set. In the mixing portion of a third set as well, there is executed a similar operation.

Figure 2:
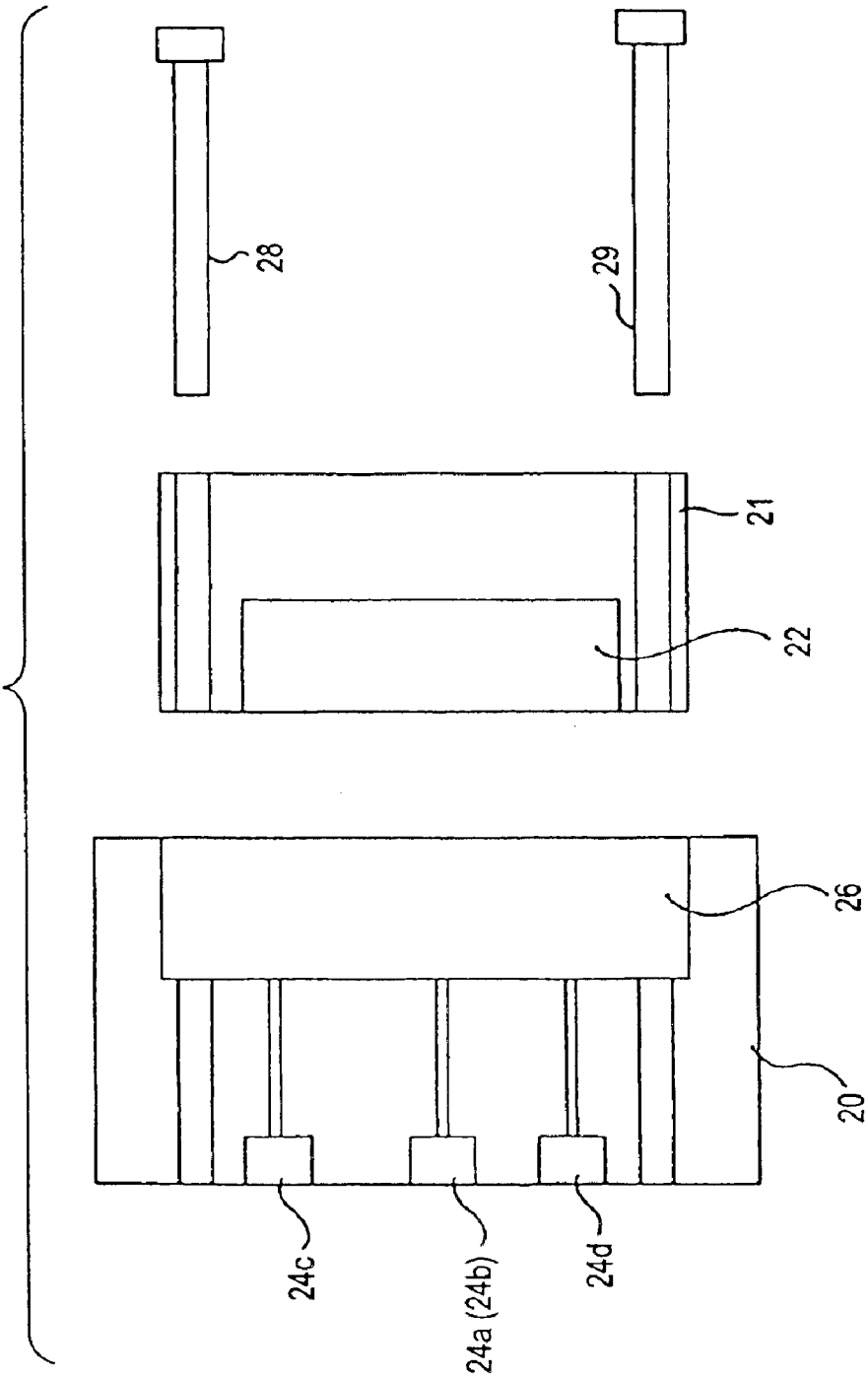
FIG. 2 is a section view of a holder on which the mixing portions can be mounted.

A plurality of sets of mixing portions, each composed of the metal plate materials 1, 5 and 12, are disposed in a holder shown in FIG. 2. The holder comprises a connecting part 20 and a support part 21. The connecting part 20 includes four connecting ports 24a–24d and a support part mounting portion 26. In the support part 21, there is formed a metal plate material mounting portion 22. After the plurality of sets of mixing portions, each composed of the metal plate materials 1, 5 and 12, are mounted on the metal plate material mounting portion 22, the support part 21 is mounted on the support part mounting portion 26 in such a manner that the connecting ports 24a–24d and penetration holes 2a–2d are matched in position to one another. Next, the connecting part 20 and support part 21 are fixed to each other using bolts 28 and 29, with the result that the metal plate materials 1, 5 and 12 provide an integrated connected body in such a manner that no bad condition such as liquid leakage can occur. The holder has a structure which can be disassembled easily and thus, when it is desired to change the capacity of the mixing portions due to variations in the flow quantities of the liquids, the metal plate materials 5 and 12 can be replaced easily.

Figure 3:
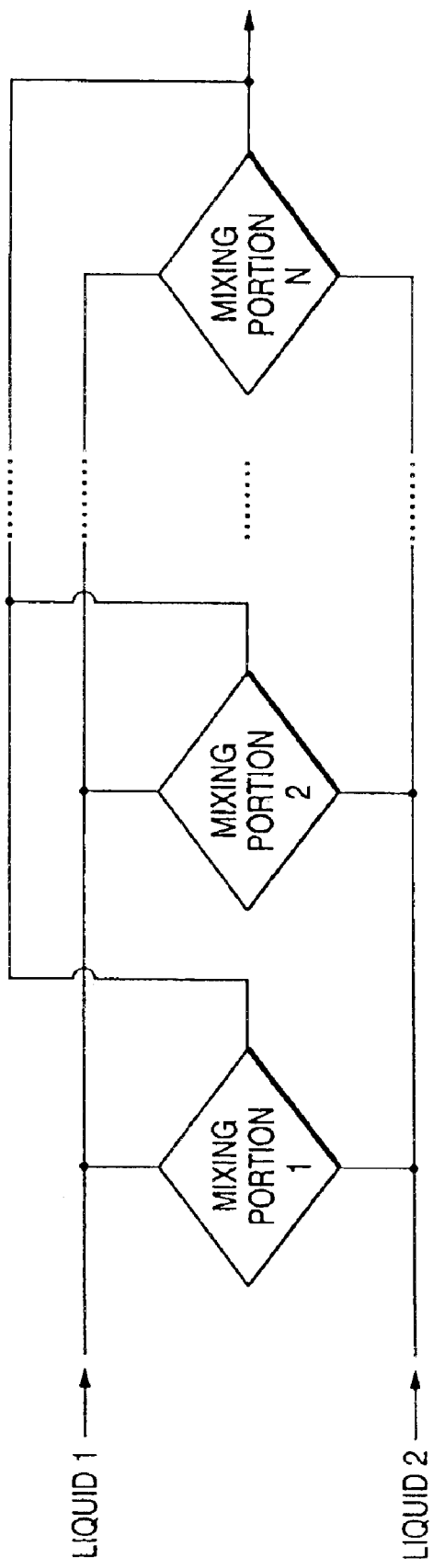
FIG. 3 is an explanatory view of a connecting method for connecting together a plurality of mixing portions.

Liquids, which that are introduced into N sets of mixing portions and are mixed together, can be taken out from the penetration holes 2c and 2d of the first set. Therefore, the respective sets are connected together in parallel as shown in FIG. 3 and thus, the liquids mixed in the respective sets are allowed to flow from the penetration holes 14c and 14d and pass through the penetration holes 6c and 6d and the penetration holes 2c and 2d, and are then allowed to meet together, so that the liquids can be mixed with high efficiency.

The flow passages 10a, 10b and 18 can be formed by etching or by press working. By changing the thicknesses of the metal plate materials 5 and 12, or by changing the widths of the grooves of the flow passages 10a, 10b and 18, the capacity of the mixing portion can be changed easily; and, the flow quantities of the liquids can be changed easily simply by replacing the metal plate materials 5 and 12.

Although description has been given heretofore of the embodiment of the invention, the invention is not limited to the above embodiment but various changes are also possible without departing from the scope of the gist of the invention as set forth in the appended patent claim. For example, the number of metal plate materials including a flow passage formed therein is not limited to a specific one but a proper number of metal plate materials can be set according to mixing flow passages to be formed. Also, the shapes of the flow passages 10a and 10b are simply the illustration examples thereof and thus the shapes of the flow passages can be designed properly so as to be able to obtain a desired mixing condition. In case where the flow passages 10a and 10b are not penetration grooves but bottomed-grooves, the metal plate material 12 can be omitted and a connected body with a mixing portion composed of the metal plate materials 1 and 5 can be formed. In this case, in the metal plate material 5, there is formed a flow passage being connected to the flow passages 10a and 10b to mix and correct the liquids flowing through the flow passages 10a and 10b.

According to the invention, there is provided a structure in which two or more plate materials each including a flow passage serving as a mixing portion are superimposed on top of each other and two or more flow passages are connected together in parallel to each other. Thanks to this, not only there can be obtained a high mixing performance but also the flow passages and the capacity of the mixing portions formed in the interior of the mixer can be changed easily. Further, since the mixer has a structure in which the plate materials are superimposed on top of each other, the number of parts can be reduced and thus the size of the mixer can be made compact.

What is claimed is:

1. A mixer for a liquid chromatograph, the mixer comprising:

a connected body including a plurality of plate materials connected together, said plurality of plate materials including first, second, and third plate materials, each of said plate materials defining a first liquid supply hole through which a first liquid flows, a second liquid supply hole through which a second liquid flows, and a liquid take-out hole through which a mixture of the first and second liquids flows out of the connected body, wherein said first liquid supply holes are in fluid communication with one another, said second liquid supply holes are in fluid communication with one another, and said liquid take-out holes are in fluid communication with one another;

wherein said second plate material also defines a first flow passage that receives the first liquid from the said second plate material first liquid supply hole and a second flow passage that receives the second liquid from the second plate material second liquid supply hole;

wherein said third plate material defines a mixing portion that receives the first liquid from the second plate material first flow passage and receives the second liquid from the second plate material second flow passage, whereby the first and second liquids mix with one another in said mixing portion and the mixture thereafter flows through the third plate material liquid take-out hole; and, wherein the first, second, and third plate material are superimposed on top of each other and wherein the flow passages are connected in parallel to each other.

2. A mixer for a liquid chromatograph according to claim 1, wherein the connected body comprises a plurality of sets of plate materials, each plate material set including said first, second, and third plate materials, and wherein the plurality of sets are connected together such that the first liquid supply holes are in a first location so as to be in fluid communication with one another, the second liquid supply holes are in a second location so as to be in fluid communication with one another, and the liquid take-out holes are in a third location so as to be in fluid communication with one another.

3. A mixer for a liquid chromatograph, the mixer comprising:
   a connected body including a plurality of plate materials, the connected body defining a first liquid supply hole, a second liquid supply hole, and a mixture take-out hole, wherein a first liquid is supplied through the first liquid supply hole, a second liquid is supplied through the second liquid supply hole, and a mixture of said first and second liquids flows out of the connected body via the mixture take out hole, and wherein the liquid supply holes and the take-out hole are formed through each of the plurality of plate materials;
   first and second supply flow passages, formed in one of said plurality of plate materials, said first supply flow passage receiving the first liquid from the first liquid supply flow hole of said one of said plurality of plate materials while said second supply flow passage receives the second liquid from the first liquid supply flow hole of said one of said plurality of plate materials;
   a mixing flow passage formed in an other of said plurality of plate materials, said mixing flow passage communicating with said first and second supply flow passages formed in said one of said plurality of plate materials so as to receive said first and second liquids therefrom, whereby said first and second liquids mix within said mixing flow passage and are communicated therefrom to said take-out holes of said other plate material and flows therethrough out of the connected body.

4. The mixer for a liquid chromatograph, according to claim 3, wherein the first and second supply flow passages are slotted openings extending through the one plate material, and wherein the mixing flow passage is a closed-bottom groove formed in the other plate material, said mixing flow passage being in direct communication with the slotted openings of the first and second supply flow passages so as to receive said first and second fluids therefrom.

5. The mixer for a liquid chromatograph according to claim 4, wherein the connected body further comprises a holder, said holder comprising:
   a support part including a plate material mounting portion for mounting the plurality of plate materials; and
   a connecting part including a support part mounting portion for mounting the support part, said connecting part defining first and second liquid input ports and a mixture output port, said first and second liquid input ports being matched in position with the first and second liquid supply holes, respectively, and said liquid output port is matched in position with the mixture take-out hole;
   wherein the plate materials are received between the support part and the connecting part.

6. The mixer for a liquid chromatograph, according to claim 5, wherein the plurality of plate materials defines a set, and wherein the set is one of a plurality of sets connected in parallel to one another and received within said holder such that the first and second liquids can be mixed with high efficiency.

7. A mixer for a liquid chromatograph, the mixer comprises a connected body including:
   a first plate material,
   a second plate material having a first supply flow passage for flowing in a first liquid and a second supply flow passage for flowing in second liquid,
   a third plate material having a mixing flow passage for collecting and mixing the first and second fluids from the first and second supply flow passages,
   wherein each of the plate materials has first and second supply penetration holes and a take-out penetration hole extending therethrough, wherein the first supply penetration hole supplies the first liquid to the first supply flow passage, the second supply penetration hole supplies the second liquid to the second supply flow passage, and the take-out penetration hole takes out a mixture of the first and second liquids from the mixing flow passage,
   wherein the plurality of plate materials are connected together in such a manner that the first supply penetration holes are coaxial with one another, said second supply penetration holes are coaxial with one another, and the take-out penetration holes are coaxial with one another.

8. The mixer for a liquid chromatograph according to claim 7, wherein the first and second supply flow passages are slotted openings extending through the second plate material, and wherein the mixing flow passage is a closed-bottomed groove formed in the third plate material, said mixing flow passage being in direct communication with the slotted openings of the first and second supply flow passages so as to receive said first and second fluids therefrom.

9. The mixer for a liquid chromatograph according to claim 8, wherein the connected body further comprises a holder for holding the plate materials, the holder comprising:
   a support part including a plate material mounting portion for mounting the plurality of plate materials; and
   a connecting part including a support part mounting portion for mounting the support part, said connecting part defining first and second liquid input ports and a mixture output port, said first and second liquid input ports being coaxial with the first and second supply penetration holes, respectively, and said liquid output port is coaxial with the take-out penetration hole;
   wherein the plate materials are received between the support part and the connecting part.

10. The mixer for a liquid chromatograph according to claim 7, wherein the plurality of plate materials defines a set, and wherein the set is one of a plurality of sets fluidly connected in parallel, so that liquids can be mixed with high efficiency.

* * * * *